United States Patent [19]

Korff et al.

[11] 4,278,819

[45] Jul. 14, 1981

[54] PROCESS FOR THE PRODUCTION OF ACETALDEHYDE DIMETHYL ACETAL

[75] Inventors: Joachim Korff, Bornheim; Max Fremery, Wesseling; Johannes Zimmermann, Weilerswist, all of Fed. Rep. of Germany

[73] Assignee: Union Rheinische Braunkohlen Kraftstoff Aktiengesellschaft, Wesseling, Fed. Rep. of Germany

[21] Appl. No.: 136,415

[22] Filed: Apr. 2, 1980

[30] Foreign Application Priority Data

Apr. 5, 1979 [DE] Fed. Rep. of Germany ....... 2913677

[51] Int. Cl.³ .................... C07C 43/303; C07C 43/30
[52] U.S. Cl. .................... 568/594; 568/882; 568/454

[58] Field of Search ................ 568/594, 909, 882, 454

[56] References Cited

U.S. PATENT DOCUMENTS

| 2,727,902 | 12/1955 | Reppe et al. | 568/594 |
| 3,631,111 | 12/1971 | Tucci | 568/909 |
| 4,190,729 | 2/1980 | Forster | 568/594 |

Primary Examiner—Werren B. Lone
Attorney, Agent, or Firm—Connolly and Hutz

[57] ABSTRACT

Improved process for the production of acetaldehyde dimethyl acetal by reacting methanol with carbon monoxide and hydrogen in the presence of a cobalt-containing catalyst, halogen or a halide as promoter and a 3-valent phosphorus compound as ligand using a nickel compound as a co-catalyst.

8 Claims, No Drawings

PROCESS FOR THE PRODUCTION OF ACETALDEHYDE DIMETHYL ACETAL

BACKGROUND OF THE INVENTION

This invention relates to a process for the production of acetaldehyde dimethyl acetal by the catalytic reaction of methanol with carbon monoxide and hydrogen in the presence of nickel and cobalt and compounds of 3-valent phosphorus as well as halogen or halides as promoter.

It is known that acetaldehyde dimethyl acetal, which is used as a starting product for the synthesis of organic oxygen containing compounds, can be obtained by catalytically reacting methanol with carbon monoxide and hydrogen. According to German Pat. No. 897,403, cobalt bromide or iodide is used as catalyst, whereas according to U.S. Pat. No. 2,727,902 quaternary cobalt complexes are used. In both cases, the reaction is carried out at elevated temperature and pressure. However, acetaldehyde dimethyl acetal cannot be economically produced by these methode on account of the long residence times of more than 30 hours which are required. Although, according to German Patent Application No. 2,625,627, acetaldehyde dimethyl acetal is obtained in the presence of cobalt iodide or cobalt acetate using tributyl phosphine as ligand with residence times of less than 5 hours, the selectivities and conversions are relatively poor.

SUMMARY OF THE INVENTION

It has now been found that the residence times in the production of acetaldehyde dimethyl acetal can be considerably shortened and hence the economy of the synthesis increased accordingly. According to the invention, acetaldehyde dimethyl acetal is obtained by the cobalt-catalysed reaction of methanol with carbon monoxide and hydrogen in the presence of halogen and/or halide as promoter at elevated temperature and pressure using a process which is characterised in that, in addition to cobalt, nickel in the form of its compounds or in the form of finely divided metal is used as co-catalyst in such a quantity that up to 1% by weight of cobalt and from 0.1 to 5% by weight of nickel are present, based on the methanol used, and the compounds of 3-valent phosphorus normally used as ligands are used as ligand in a molar ratio of nickel to ligand of from 5:1 to 1:3, the reaction being carried out at temperatures in the range from 180° to 230° C., under pressures of from 200 to 500 bars and with a ratio of CO to $H_2$ of from 2:1 to 1:2.2.

It has been found to be of advantage to work in the liquid phase using dissolved catalyst. However, the catalyst may also be used in insoluble form, for example in the form of finely divided metal or on a support material. The reaction may also be carried out in the gas phase. Solvents are not necessary for the reaction according to the invention, although they may be used, for example hydrocarbons, such as heptane or toluene.

DETAILED DESCRIPTION OF THE INVENTION

The cobalt and nickel compounds used are salts, such as bromides, iodides, acetates, formates, propionates, which react with carbon monoxide to form cobalt carbonyl or hydrocobalt carbonyl complexes. The proportion of cobalt in the catalyst system may be considerably reduced and may be smaller than the proportion of nickel. Up to around 1% by weight and preferably from about 0.001 to 0.5% by weight of cobalt is used, based on methanol. The quantity of nickel generally amounts to between about 0.1 and 5% by weight and more particularly to between 0.15 and 3% by weight, based on the methanol used.

The ligands used are normally used compounds such as 3-valent phosphorus compounds corresponding to the following formula

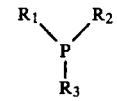

in which $R_1$, $R_2$ and $R_3$ may be for example alkyl, aryl or aralkyl groups. However, many other groups, such as for example bicyclic compounds in which P is incorporated as a hetero atom, phenoxy or alkoxy groups, are also suitable for the reaction. It has proved to be of advantage to use triphenyl phosphine for example.

The promoters used for the reaction are halides, particularly hydrogen iodide or bromide and also methyl iodide or methyl bromide. However, elemental iodine or bromine may also be used. Very good results are also obtained with iodides or bromides of nickel, cobalt or cesium and also with mixtures of the compounds mentioned. Based on the nickel used, iodine and/or bromine is/are used in a quantity of from 0.1 to 3 molar and preferably in a quantity of from 0.25 to 1 molar.

The reaction is carried out at temperatures in the range from 180° to 230° C. and under pressures of from about 200 to 500 bars, although it can be of advantage to apply even higher pressures. Preferred reaction conditions are temperatures of from 190° to 210° C. and pressures of from 280 to 320 bars. The reaction is carried out using ratios of carbon monoxide to hydrogen of from 2:1 to 1:2,2, the preferred ratio being 1:1. The yield of acetaldehyde dimethyl acetal is not adversely affected if the starting gas contains small inert fractions such as $CO_2$, $H_2$ or $CH_4$. Accordingly, the usual synthesis gas quality may be used.

In the process according to the invention, the residence times of more than 30 hours required in the known processes may be shortened, in some cases to less than one hour. The preferred residence times are from 5 minutes to 2 hours, depending on whether the process is carried out in batches or continuously.

The reaction product contains only small quantities of secondary products and may be worked up by distillation in the usual way. The percentages quoted in the Examples represent percent by weight.

EXAMPLE 1

A stirrer-equipped autoclave of Hastelloy C was filled with 405 g (12.6 moles) of methanol, 10 g (0.04 mole) of Ni-(acetate)$_2$.4H$_2$O, 4.8 g of HI, 0.8 g of Co(acetate)$_2$.4H$_2$O (8%, based on Ni) and 40 mMoles of triphenyl phosphine. After the system had been purged with nitrogen, a CO/H$_2$ (1:1)-mixture was introduced under pressure up to a pressure of 290 bars. After the reaction temperature of 200° C. had been reached, a fresh CO/H$_2$(1:1)-mixture was continuously added during the 1-hour reaction time so that the pressure of 290 bars was maintained. After the autoclave had been cooled and the reaction product worked up by distillation, it was found that 57.9% of the methanol used had reacted with a selectivity of 79.6% to form acetaldehyde dimethyl acetal. In addition, 8.6% of acetaldehyde and 5.8% of methyl acetate were obtained.

EXAMPLE 2

The reaction was carried out in the same way as in Example 1 except that, instead of 8%, 4% of cobalt was used. The conversion amounted to 49.9% for a selectivity of 82.6%. 5.0% of acetaldehyde and 8.6% of methyl acetate were obtained as secondary products.

EXAMPLE 3

The reaction was carried out in the same way as in Example 1 except that 16% of cobalt, based on nickel, was used. Under these conditions, the conversion rose to 67.8% whereas selectivity fell to 63.7% of acetaldehyde dimethyl acetal.

EXAMPLE 4

The reaction was carried out in the same way as in Example 1 except that the residence time was 30 minutes. The conversion amounted to 43% whereas selectivity rose to 82.0% of acetaldehyde dimethyl acetal. In addition, 3.7% of acetaldehyde and 10.6% of methyl acetate were obtained.

EXAMPLE 5

The reaction was carried out in the same way as in Example 2 except that, instead of triphenyl phosphine, 40 mMoles of tributyl phosphine were used. The conversion amounted to 45.5% for a selectivity of 82.8%. In addition, 3.6% of acetaldehyde and 5.3% of methyl acetate were obtained.

EXAMPLE 6

The reaction was carried out in the same way as in Example 2 except that only 20 mMoles of triphenyl phosphine were used. The conversion amounted to 44.2% for a selectivity of 83.7%.

We claim:

1. A process for the production of acetaldehyde dimethyl acetal by the cobalt-catalysed reaction of methanol with carbon monoxide and hydrogen in the presence of a promoter selected from the group consisting of iodine, bromine, an iodide of hydrogen, methyl, nickel, cobalt, cesium and a bromide of hydrogen, methyl, nickel, cobalt, cesium at elevated temperature and pressure, which comprises using, in addition to cobalt, nickel in the form of its compounds capable to build a carbonyl- or a hydrocarbonyl complex or in the form of finely divided metal as co-catalyst in such a quantity that up to 1% by weight of cobalt and from 0.1 to 5% by weight of nickel are present, based on the methanol used, and the compounds of 3-valent phosphorus normally used as ligands are used as ligand in a molar ratio of nickel to ligand of from 5:1 to 1:3, the reaction being carried out at temperatures in the range from 180° to 230° C., under pressures of from 200 to 500 bars and with a ratio of CO to $H_2$ of from 2:1 to 1:2.2.

2. A process as claimed in claim 1 wherein the reaction is carried out in the liquid phase.

3. A process as claimed in claim 1 wherein salts of nickel and cobalt which are soluble in the reaction medium are used.

4. A process as claimed in claim 1 wherein the cobalt is used in a quantity of from 4 to 16% by weight, based on the nickel used.

5. A process as claimed in claim 1 wherein the nickel is used in a quantity of from 0.15 to 3% by weight, based on the methanol used.

6. A process as claimed in claim 1 wherein triphenyl phosphine is used as ligand.

7. A process as claimed in claim 1 wherein methyl iodide or methyl bromide is used as promoter.

8. A process as claimed in claim 1 wherein hydrogen iodide or hydrogen bromide is used as promoter.

* * * * *